US010328626B2

(12) United States Patent
Erhard et al.

(10) Patent No.: US 10,328,626 B2
(45) Date of Patent: Jun. 25, 2019

(54) TUBE MAT, METHOD FOR PRODUCING SAID TUBE MAT AND TOOL FOR EXTRUDING THE TUBE MAT

(71) Applicant: Raumedic AG, Münchberg (DE)

(72) Inventors: Dominik Erhard, Kulmbach (DE); Martin Stöcker, Helmbrechts (DE)

(73) Assignee: Raumedic AG, Münchberg (DE)

( * ) Notice: Subject to any disclaimer, the term of this patent is extended or adjusted under 35 U.S.C. 154(b) by 298 days.

(21) Appl. No.: 14/412,601

(22) PCT Filed: Jun. 12, 2013

(86) PCT No.: PCT/EP2013/062087
§ 371 (c)(1),
(2) Date: Jan. 2, 2015

(87) PCT Pub. No.: WO2014/005809
PCT Pub. Date: Jan. 9, 2014

(65) Prior Publication Data
US 2015/0147522 A1    May 28, 2015

(30) Foreign Application Priority Data

Jul. 4, 2012  (DE) .................... 10 2012 211 617

(51) Int. Cl.
*A61M 1/16*   (2006.01)
*B01D 69/08*  (2006.01)
(Continued)

(52) U.S. Cl.
CPC ........... *B29C 48/11* (2019.02); *A61M 1/1627* (2014.02); *A61M 1/1629* (2014.02);
(Continued)

(58) Field of Classification Search
CPC .............. A61M 1/1627; A61M 1/1629; A61M 1/1698; B01D 69/08; B01D 69/082; B01D 63/02; B01D 63/021; B01D 63/025; B01D 69/04; Y10T 428/24744; F28F 1/22; F28F 1/16; F28F 1/10; F28F 1/14; F28F 9/0202; F28D 7/0041; F28D 7/1623; F28D 7/16;
(Continued)

(56) References Cited

U.S. PATENT DOCUMENTS 3,015,136 A  *  1/1962  Doe .................... A47G 27/0218
                                                  15/239
3,205,563 A  *  9/1965  Pauls .................. B21D 53/045
                                                  29/890.042
(Continued)

FOREIGN PATENT DOCUMENTS

DE    1 808 271    4/1970
DE    27 04 678    8/1977
(Continued)

OTHER PUBLICATIONS

Search Report dated Feb. 18, 2013 in corresponding DE 10 2012 211 617.6.

*Primary Examiner* — Catherine A. Simone
(74) *Attorney, Agent, or Firm* — Boyle Fredrickson S.C.

(57) ABSTRACT

A tube mat comprises a plurality of tube portions having a tube longitudinal axis in each case and at least one web portion connecting two tube portions, the tube mat being produced in one piece.

25 Claims, 7 Drawing Sheets

(51) Int. Cl.
- *B29C 48/30* (2019.01)
- *B29C 48/11* (2019.01)
- *B29C 47/00* (2006.01)
- *B29C 47/20* (2006.01)
- *B29C 48/32* (2019.01)
- *B29K 75/00* (2006.01)

(52) U.S. Cl.
CPC .......... *A61M 1/1698* (2013.01); *B01D 69/08* (2013.01); *B29C 47/0028* (2013.01); *B29C 47/20* (2013.01); *B29C 48/30* (2019.02); *B29C 48/32* (2019.02); *B29K 2075/00* (2013.01); *B29K 2883/005* (2013.01); *Y10T 428/24273* (2015.01); *Y10T 428/24479* (2015.01); *Y10T 428/24744* (2015.01)

(58) Field of Classification Search
CPC . D01D 5/24; A47L 23/22; A47L 23/24; A47L 23/26; A47L 23/266; B21D 53/06; B21D 53/08; B29C 48/11; B29C 48/30; B29C 48/32; B29C 47/20; B29C 47/0028
See application file for complete search history.

(56) References Cited

U.S. PATENT DOCUMENTS

| | | | | |
|---|---|---|---|---|
| 3,404,446 A | * | 10/1968 | Kritzer | B21C 37/225 165/181 |
| 4,267,681 A | * | 5/1981 | Dickson | A47G 27/02 52/664 |
| 4,273,070 A | | 6/1981 | Hoefelmayr | |
| 4,296,539 A | * | 10/1981 | Asami | F16L 9/19 165/115 |
| 4,332,752 A | | 6/1982 | Henne et al. | |
| 5,063,009 A | | 11/1991 | Mizutani | |
| 5,186,022 A | * | 2/1993 | Kim | F25B 39/02 165/64 |
| 5,511,965 A | | 4/1996 | Batdorf et al. | |

FOREIGN PATENT DOCUMENTS

| | | |
|---|---|---|
| DE | 28 38 659 | 2/1980 |
| DE | 43 04 246 | 8/1994 |
| DE | 35 87 787 | 10/1994 |
| GB | 2 268 635 | 1/1994 |
| WO | 94/17979 | 8/1994 |
| WO | 2012/040778 | 4/2012 |

* cited by examiner

TUBE MAT, METHOD FOR PRODUCING SAID TUBE MAT AND TOOL FOR EXTRUDING THE TUBE MAT

CROSS-REFERENCE TO RELATED APPLICATIONS

This application claims the priority of German Patent Application, Serial No. 10 2012 211 617.6, filed Jul. 4, 2012, pursuant to 35 U.S.C. 119(a)-(d), the content of which is incorporated herein by reference in its entirety as if fully set forth herein.

FIELD OF THE INVENTION

The invention relates to a tube mat, a method for producing a tube mat of this type and a tool for extruding a tube mat of this type.

BACKGROUND OF THE INVENTION

A tube arrangement for a quarter milking machine is known from DE 28 38 659 C2. The tube arrangement has four tube lines running parallel to one another, which lie at the corners of a rhombus. The tube arrangement is not a tube mat.

DE 35 87 787 T2 discloses a method for producing hollow fibres by means of melt spinning. Specially configured spinning nozzles are necessary for this. Hollow fibres produced from plastics material are wetted with a spinning liquid. A method of this type is complex.

Tubes, which can have reinforcement elements such as ribs for stability reasons, are known from DE 18 08 271 A1. A method for producing a tube is known from DE 43 04 246 A1. A tube mat is not known from DE 43 04 246 A1.

DE 27 04 678 A1 discloses a method for extruding a plastics material net.

During an open heart operation, blood from a patient is extracorporeally supplied with oxygen in a heart-lung machine and carbon dioxide is simultaneously removed. This is so-called extracorporeal circulation (ECC). A similar blood treatment is also used in an extracorporeal membrane oxygenation (ECMO) for the pulmonary support of a lung patient. In both cases, hollow fibre bundles are used, oxygen and blood, separately from one another in each case, being guided through the lumina formed by the hollow fibres or through the gaps of the hollow fibres.

A hollow fibre bundle of this type is known from DE 10 2010 000 820 A1. A plurality of tube portions are arranged with their tube longitudinal axes parallel to one another and knitted together by means of at least one knitting seam in a direction perpendicular to the tube longitudinal axes.

SUMMARY OF THE INVENTION

An object of the present invention is to further develop a tube mat in such a way that it can be produced in a simplified manner.

This object is achieved according to the invention by a tube mat having a plurality of tube portions in each case having a tube longitudinal axis, at least one web portion connecting two tube portions, and at least one spacer, which has a thickness, which is oriented perpendicular to a mat plane and is greater than an external diameter of a tube portion, wherein the tube mat is produced in one piece, and wherein the spacer is arranged on a web portion between two adjacent tube portions, and the spacer, along the tube longitudinal axis, has a length, which is smaller than a length of the tube portions.

The tube mat according to the invention is produced in one piece. In particular, it is unnecessary to produce a plurality of tube portions individually, to arrange them in a defined manner in relation to one another and to then knit them together. Owing to the one-piece production of the tube mat, tube portions are automatically arranged in a defined manner in relation to one another and connected to one another. In particular, the tube mats are arranged with their tube longitudinal axes parallel to one another in each case. The tube portions are connected to one another in each case by a web portion. The production of the tube mat according to the invention is simplified. In particular, the number of method steps is reduced. The number of individual parts is reduced, so the assembly outlay for the tube mat is dispensed with. The assembly outlay for the production of a heat exchanger is thereby reduced in total. The time outlay and the cost outlay for producing the tube mat according to the invention are reduced. In particular, the tube mat can be produced in one piece by extrusion. The risk of contamination during the production of the tube mat is minimised as, in particular, knitting with knitting threads and therefore an introduction of dust and/or fibre abrasion is ruled out. The tube mat, with regard to its application, has an increased reliability. The reject rate during the production of the tube mat is reduced. The risk of unnoticed contamination of the tube mat leading to the endangering of the health of a patient is reduced. Tube mats of this type can be used both in an oxygenator for extracorporeal circulation (ECC) and for extracorporeal membrane oxygenation (ECMO). The tube mat is basically also suitable for use in the pharmaceutical industry sector for so-called bioreactors. For example, fermenters are known, in which a bacteria culture in solution is provided with oxygen by hollow fibres. Hollow fibres of this type may be represented by the tube mats. It is also known to use oxygenation fibres in tissue engineering. The tube mats may also be used as heat exchanger mats, for example in floor heating, wall heating and/or corresponding cooling elements. The tube mat according to the invention is configured to be substantially flat as a mat in a starting arrangement. This means that the longitudinal axes of the tube portions can be arranged in a mat plane. It is possible to roll up the tube mat individually of with at least one further tube mat to form a tube mat bundle, so, in particular, a substantially cylindrical tube mat bundle results.

A tube mat with at least one spacer, which has a thickness, which is oriented perpendicular to a mat plane and is greater than an external diameter of a tube portion, allows simplified production of a tube bundle of a plurality of tube mats. Owing to the at least one spacer, the tube portions of a tube mat may be arranged at a defined spacing with respect to one another. In particular, a plurality of tube mats are rolled up or wound up to form a tube bundle.

A tube mat, in which the spacer is arranged on a tube portion, allows a flexible connection of the tube mats to form a tube mat bundle.

A tube mat having a plurality of spacers along the tube longitudinal axis allows a connection of individual tube mats to one another with an increased strength. Individual spacers may, in particular, engage in corresponding gaps of another tube mat during the connection of the individual tube mats to one another. The use of material for the production of the spacers along the tube longitudinal axis is reduced in relation to a continuous, web-shaped spacer.

A tube mat, in which the spacer, along the tube longitudinal axis, has a length, which is substantially the same size as a length of the tube portions, has an increased moment of inertia of area with respect to a bend about a direction directed transversely to the tube longitudinal axes. The tube mat is stable. In particular, the spacers are configured as continuous webs. Webs of this type can be produced in a simplified manner.

A tube mat, in which the spacer has a cross sectional face, which is oriented perpendicular to the tube longitudinal axis and has a circular or star-shaped contour, allows an improved connection to another tube mat to form a tube mat bundle.

A tube mat having at least one recess arranged in a web portion allows a material saving during production. In addition, a tube mat of this type has an increased diffusion surface.

A tube mat produced from silicone rubber or polyurethane can be produced in a simplified manner. Since a plurality of tube portions are extruded at the same time as a one-piece component in the form of the tube mat, the mat overall can be drawn off better during the extrusion. The risk of tearing individual silicone tube portions is reduced. The production of the tube mat can be carried out in a reliable manner. A tube mat of this type is, in particular, suitable for use in an oxygenator module during the ECC. Alternatively, it is also possible to use polyurethane or other thermoplastic polymers to produce the tube mat. In this case, the tube mat can also be used for heat exchangers in general.

A further object of the present invention is to simplify a method for producing a tube mat.

This object is achieved by a method for producing a tube mat comprising the method steps providing a tool for extruding a tube mat along an extrusion direction, extruding a tube mat with a plurality of tube portions arranged along the extrusion direction and at least one web portion connecting two tube portions.

In a method for producing a tube mat, a tool is firstly provided, with which a tube mat can be extruded along an extrusion direction. An extrusion of the tube mat, which has a plurality of tube portions arranged along the extrusion direction and at least one web portion connecting two tube portions, then takes place. As a result it is possible to produce a plurality of tube portions, which are in each case connected to one another by web portions, in one piece in one method step by extrusion. A method of this type is economical. Since a plurality of tube portions are connected to one another by the web portions, a tube mat with improved structural stability is produced. In particular, the tube mat can be drawn off better from the extrusion tool. In particular, the handling is also improved for possible downstream method steps. In particular, a tube mat produced in this manner can be better deposited and/or wound. For example, a plurality of tube mats can be connected to form a tube bundle, in that, in particular, a tube portion of a first tube mat is arranged on a web portion of a second tube mat and these are then connected by rolling to form a tube bundle.

A further object of the present invention is to provide a tool for extruding a tube mat.

This object is achieved by a tool for extruding a tube mat along an extrusion direction comprising an extrusion nozzle having a mat cavity, wherein the mat cavity comprises a plurality of tube cavities having a longitudinal axis in each case and arranged parallel to the extrusion direction and at least one web cavity connecting two adjacent tube cavities in each case, and a mandrel arranged in a tube cavity in each case.

A tool of this type is used for extruding a tube mat along an extrusion direction. The tool has an extrusion nozzle, which can be connected to an extrusion chamber. The plastics material melt to be extruded can be stored in the extrusion chamber. The extrusion nozzle has a mat cavity, which comprises a plurality of tube cavities having a longitudinal axis in each case and arranged parallel to the extrusion direction as well as at least one web cavity connecting two adjacent tube cavities in each case. A mandrel is arranged in each tube cavity so that a substantially annular gap is formed between an outer wall of the mandrel and an inner wall of the tube cavity. As a plurality of tube cavities are provided, a plurality of mandrels is also comprised by the tool.

Embodiments of the invention will be described in more detail below with the aid of the drawings.

DESCRIPTION OF THE PREFERRED EMBODIMENTS

Figure 1:
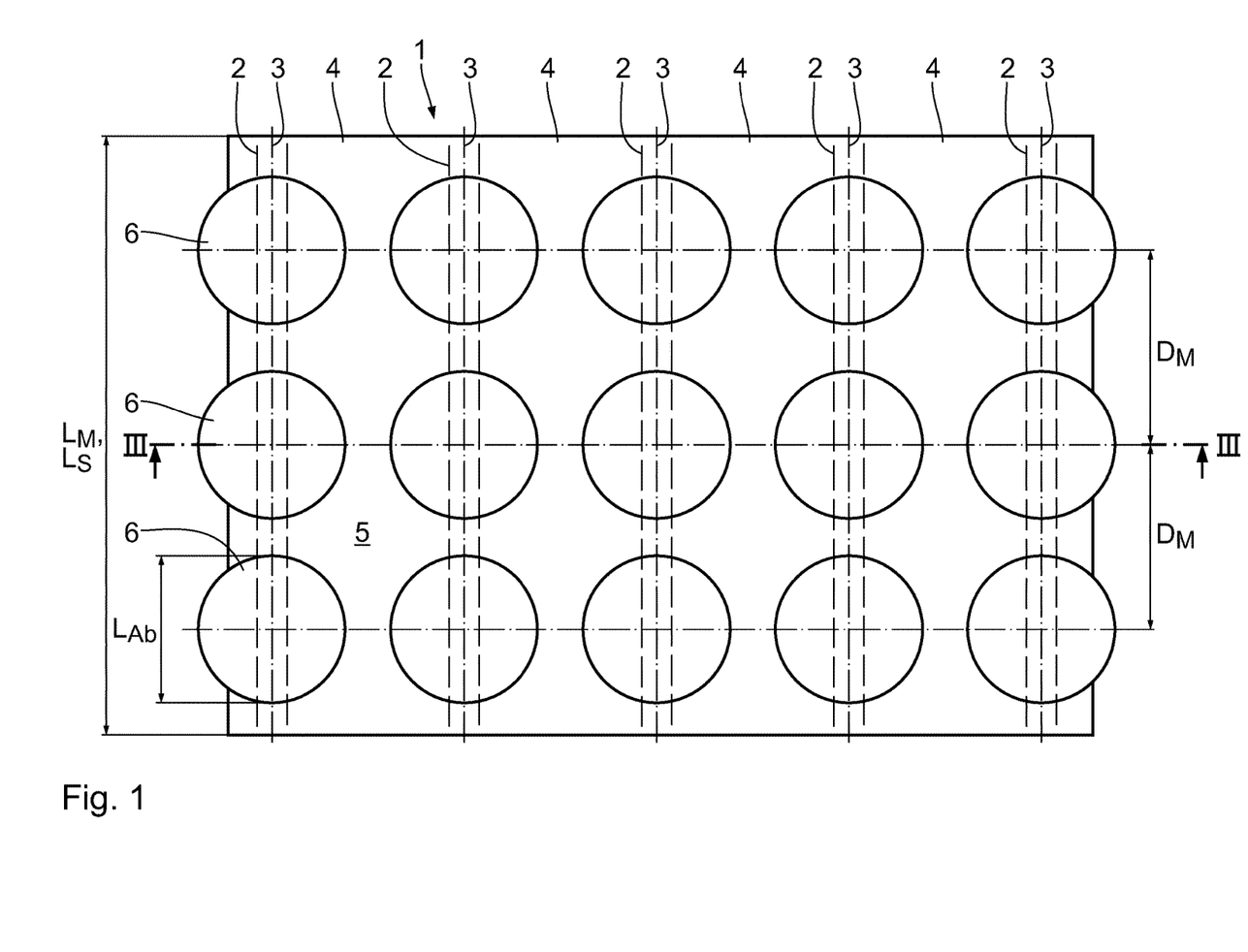
FIG. 1 shows a plan view of a tube mat according to the invention.
Figure 2:
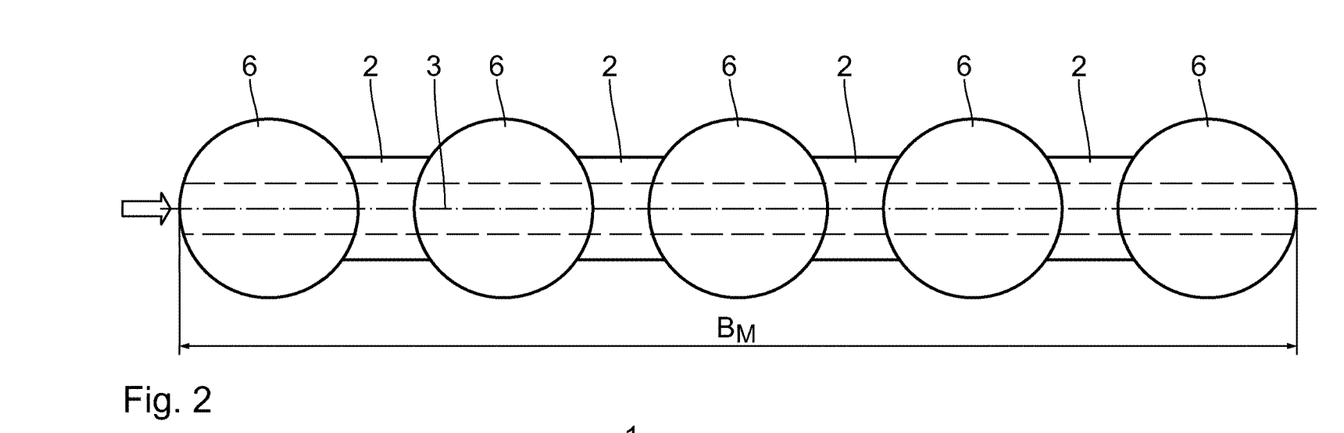
FIG. 2 shows a side view of the tube mat in FIG. 1.
Figure 3:
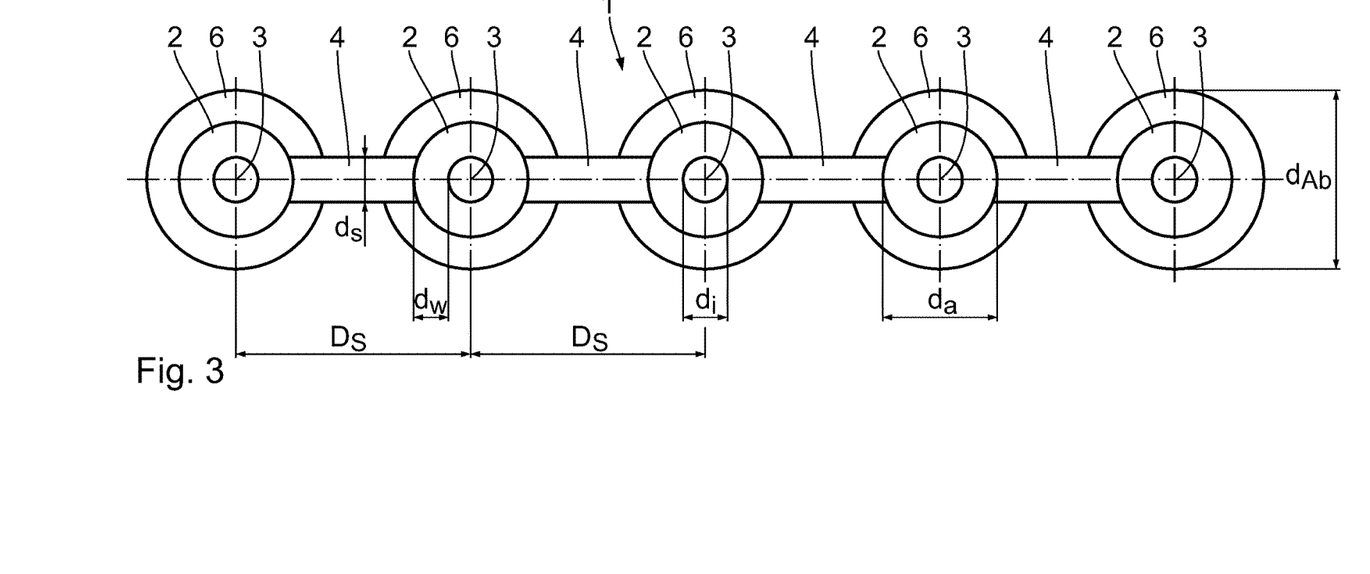
FIG. 3 shows a sectional view along the line III-III in FIG. 1.

A tube mat 1 shown in FIGS. 1 to 3 has five tube portions 2. The tube portions 2 are in each case oriented with their tube longitudinal axis 3 parallel to one another. Two respective tube portions 2 are in each case connected to one another by a web portion 4. According to the embodiment shown, five tube portions 2 and four web portions 4 are thus provided.

Each tube portion 2 has a tube wall with a tube wall thickness $d_w$ in the range from 10 µm 200 µm, preferably between 10 µm and 50 µm. An internal diameter $d_i$ of a tube portion 2 is between 10 µm and 1,000 µm, preferably between 10 µm and 500 µm. Accordingly, an external diameter $d_a$ of a tube portion is between 30 µm and 1,400 µm.

The web portion 4 has a thickness $d_S$ of about 10 µm to 200 µm. The thickness $d_S$ of the web portion 4 is oriented perpendicular to a mat plane 5. The mat plane 5 corresponds to the plane of the drawing in FIG. 1.

More or less than the five tube portions 2 shown in FIGS. 1 to 3 per tube mat 1 are also possible. The number, the size of the tube portions 2 and the number and the size of the web portions 4 depend on the purpose of use of the tube mat 1. In particular, the number of tube portions 2 of a tube mate 1 is more than 10.

The tube mat 1 has a length $L_M$, which is identical to a length $L_S$ of the individual tube portions 2. The length $L_S$ of the tube portions 2 is oriented parallel to the tube longitudinal axis 3. Furthermore, the tube mat 1 has a width $B_M$.

The length $L_M$ of the tube mat 1 is, in particular, between 5 cm and 30 cm depending on the purpose of use of the oxygenator. For example, the length $L_M$ is 5 cm in a tube mat 1 for an oxygenator of a premature baby or, for example, 30 cm for an oxygenator of an adult person. During production, the length $L_M$ of the tube mat 1 is not limited. In particular when the tube mat 1 is produced as described below by extrusion, any length $L_M$ can be provided. It is possible to provide the tube mat 1 as a joined product, so that tube mats 1 with a predetermined length $L_M$ or with various lengths can be cut to size at a later time. The width $B_M$ is preferably between 2 cm and 50 cm. The width $B_M$ is, in particular, also determined by the dimensions of the tube portions 2 and by a tool for producing the tube mat 1.

The tube mat 1 is produced in one piece from silicone rubber. The tube mat 1 has a uniform, homogeneous material. The tube mat 1 has homogeneous material properties. Three spacers 6 are provided in each case along the tube longitudinal axis 3 on the tube portions 2. The spacers 6 are configured as spherical thickenings. The spacers 6 are in each case formed from silicone rubber in one piece with the tube mat 1. The spacers 6 have a round cross sectional face oriented perpendicular to the tube longitudinal axis 3. The spacers 6 have a thickness $d_{Ab}$, which is oriented perpendicular to the mat plane 5 and is about 40 μm to 2,000 μm.

The tube mat 1 is produced by extrusion. It is conceivable to produce the tube mat 1 by means of coextrusion and, in particular, to produce the tube portions 2 and the web portions 4 from a first material and the spacers 6 from a second material that is different from this by coextrusion.

According to the embodiment shown, a length $L_{Ab}$ of the spacers 6 along the tube longitudinal axis 3 is identical to the thickness $D_{Ab}$. In particular, the length $L_{Ab}$ is smaller than the length $L_S$ of the tube portion 2. The thickness $D_{Ab}$ of the spacer 6 is greater than the external diameter $d_a$ of the tube portion 2. The typical structure of the tube mat 1 shown in FIG. 3 corresponds to that of a chain of pearls. In the embodiment of the tube mat 1 in FIGS. 1 to 3, the spacers 6 are arranged along the tube portions 2. A centre spacing $D_M$ of the spacers 6 along the tube longitudinal axis 3 is identical. The spacers 6 are arranged regularly, i.e. with a constant centre spacing $D_M$, along the tube portions 2. The tube portions 2 are arranged regularly, i.e. with identical tube portion spacings $D_S$, in a direction perpendicular to the tube longitudinal axes 3. In the embodiment, the spacers 6 are arranged in a regular, rectangular grid. A grid spacing along the tube longitudinal axis 3 is the centre spacing $D_M$. A grid spacing in a direction oriented perpendicular to the tube longitudinal axes 3 is the tube portion spacing $D_S$. It is also conceivable for the spacings $D_M$ and/or $D_S$ to vary in a tube mat 1.

The spacers 6 are arranged perpendicular to one another between adjacent tube portions 2, i.e. an imaginary connecting line of two spacers 6 of adjacent tube portions 2 is oriented perpendicular to the tube longitudinal axes 3 like, for example, the section line III-III. The characteristic pearl chain structures resulting therefrom are identical along the tube longitudinal axis 3.

According to a further embodiment, not shown, of a tube mat 1, the spacers 6 may in each case be arranged along a tube portion 2, the spacers 6 of two adjacent tube portions 2 along the tube longitudinal axes 3 being arranged offset with respect to one another. In particular, it is conceivable to select the tube portion spacing $D_S$ and the centre spacing $D_M$ in such a way that all the spacers 6 of the tube mat 1 are arranged pairwise with respect to one another with the same spacing. In particular, the spacers 6 may be arranged in such a way that three adjacent spacers 6 form the corner points of an equilateral triangle. As a result, it is possible to enable a tube mat 1 with a densest surface arrangement of the spacers. As a result, it is possible to enable a higher surface density of the spacers 6, in other words, to increase the number of spacers 6 per area.

It is also conceivable to make the pearl chain structure variable along the tube longitudinal axes 3.

Figure 4:
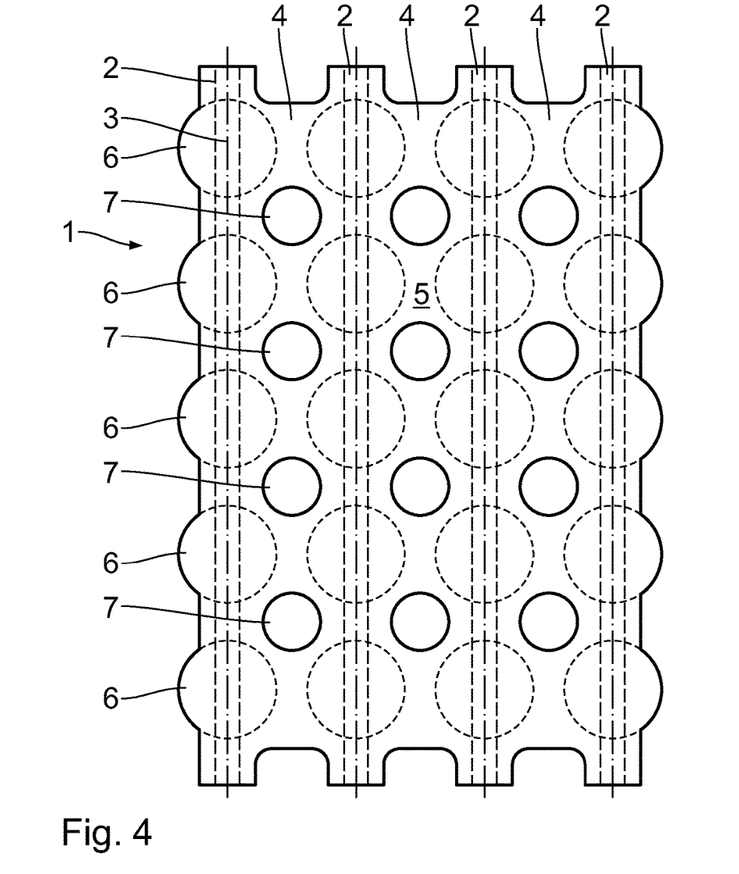
FIG. 4 shows a plan view, corresponding to FIG. 1, of a tube mat according to a further embodiment.

FIG. 4 shows a further configuration of a tube mat 1. Components, which correspond to those, which have been described above with reference to FIGS. 1 to 3, have the same reference numerals and will not be discussed again in detail.

The tube mat 1 according to FIG. 4 substantially corresponds to the tube mat 1 according to FIG. 1, four tube portions 2 and three web portions 4 being provided. Five spacers 6 are provided on each tube portion 2 along the tube longitudinal axis 3. The important difference of the tube mat 1 according to FIG. 4 compared to the tube mat 1 in FIG. 1 is a plurality of recesses 7. The recesses 7 have a circular contour, oval contour or rectangular contour with rounded edges in the mat plane 5. The recesses 7 are arranged in a direction parallel to the tube longitudinal axis 3 between two adjacent spacers 6 and in a direction perpendicular to the tube longitudinal axes 3 between two adjacent tube portions 2. The recesses 7 penetrate the web portions 4 completely. The recesses 7 are holes.

Figure 5:
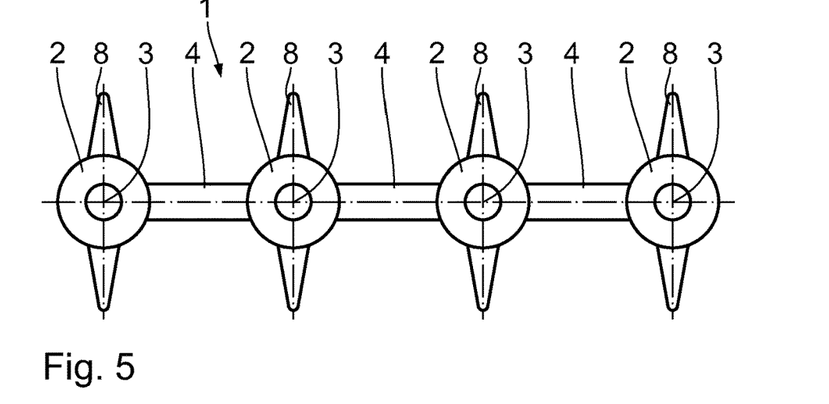
FIG. 5 shows a sectional view, corresponding to FIG. 3, of a further embodiment of a tube mat.
Figure 6:
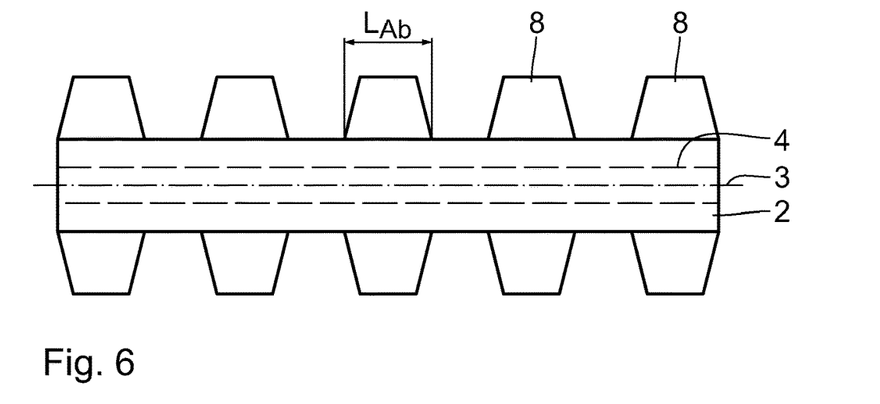
FIGS. 6, 7 show side views, corresponding to FIG. 2, of further embodiments of a tube mat.
Figure 7:
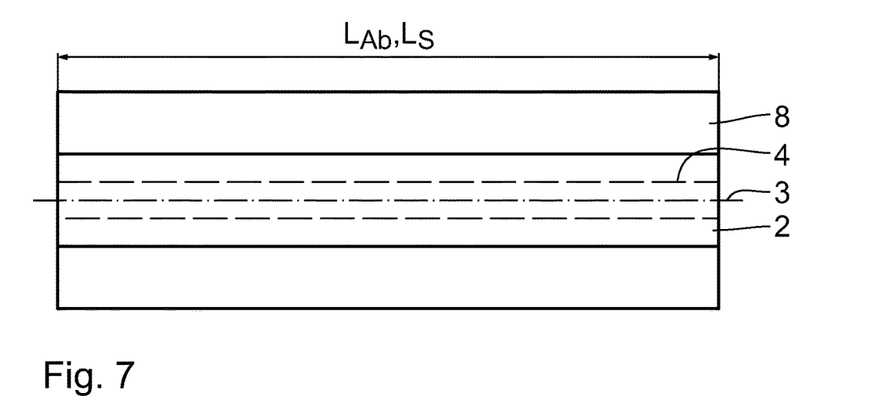

FIGS. 5 to 7 show further configurations of a tube mat 1. Components, which correspond to those, which have been described above with reference to FIGS. 1 to 4, have the same reference numerals and will not be discussed again in detail.

The tube mat 1 according to FIGS. 5 to 7 substantially differs from the previous tube mats by the configuration of the spacers 6. The spacers 8 have a cross sectional face oriented perpendicular to the tube longitudinal axis 3 with a star-shaped contour. The spacers 8, corresponding to the spacers 6, may have a reduced length $L_{Ab}$ along the tube longitudinal axis 3 (FIG. 6). It is also possible for precisely one spacer 8 to be provided along the tube longitudinal axis 3. In this case, the spacer 6 has a length $L_{Ab}$, which is identical to the length $L_S$ of the tube portion 2 (FIG. 7).

Figure 8:
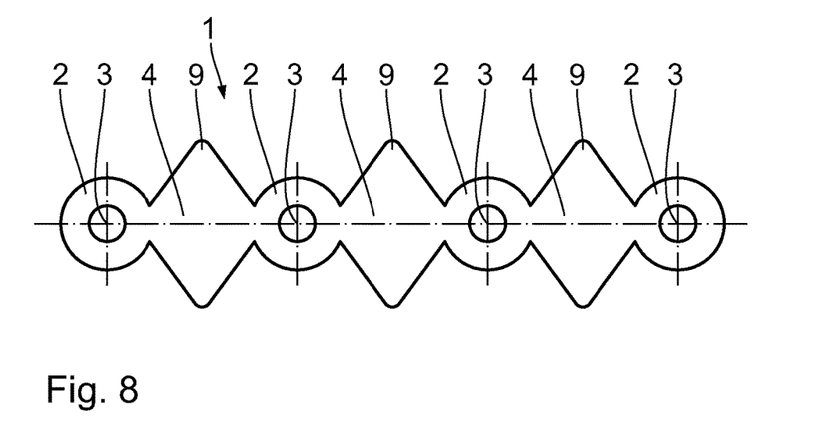
FIG. 8 shows a sectional view, corresponding to FIG. 3, of a further embodiment of a tube mat.

FIG. 8 shows a further configuration of a tube mat 1. Components, which correspond to those, which have been described above with reference to FIGS. 1 to 7, have the same reference numerals and will not be discussed again in detail.

The tube mat 1 differs from the previous tube mats in that the spacers 9 are arranged on the web portions 4. In particular, the tube portions 2 are free of spacers. The spacers 9 are configured in a star shape similarly to the spacers 8 according to the tube mat 1 in FIG. 5.

According to a further embodiment, not shown in the figures, it is possible to provide a plurality of differently shaped spacers on a tube mat. It is possible to provide the spacers both in the region of the tube portions and in the region of the web portions. The spacers may either have a reduced length $L_{Ab}$ and/or a length $L_{Ab'}$, which substantially corresponds to the length $L_S$ of the tube portion 2.

Figure 9:
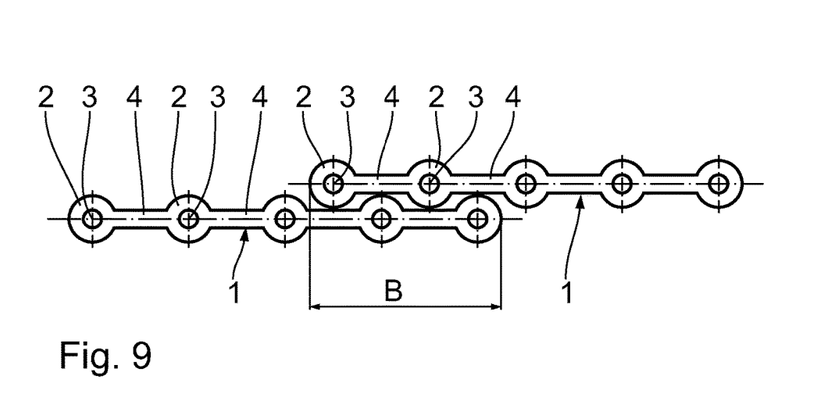
FIGS. 9, 10 show schematic views for the arrangement of a plurality of tube mats for producing a tube bundle.
Figure 10:
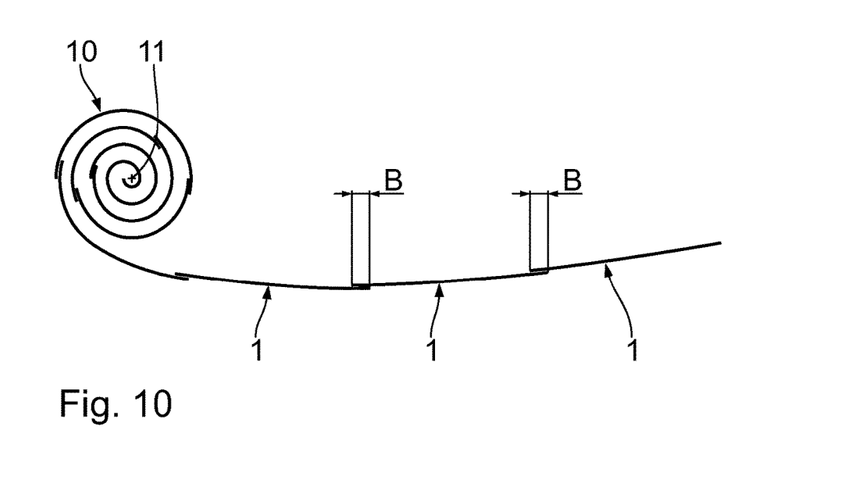

A method for producing a tube bundle 10 will be described in more detail below with reference to FIGS. 9 and 10. The tube bundle 10 has a bundle longitudinal axis 11. The tube bundle 10 is roll-shaped and has a circular cross section oriented perpendicular to the bundle longitudinal axis 11. The bundle longitudinal axis 11 is oriented parallel to the tube longitudinal axes 3.

To produce the tube bundle 10, a plurality of tube mats 1 are connected to one another and then rolled to form the bundle 10. The number of tube mats 1, which are rolled to form a tube bundle 10, depends on the respective width $B_M$ of the tube mats 1 and the purpose of use of the tube bundle 10 produced therewith. The individual tube mats 1 are schematically shown in FIG. 10. In particular, the exact cross sectional contour of a tube mat, which is produced from the tube portions 2 connected to one another by the web portions, is not shown in detail. This contour is shown in FIG. 9. It emerges from this that a further, second tube mat 1 is arranged on a first tube mat 1 shown at the bottom left in FIG. 9. The further tube mat 1 is shown at the top right in FIG. 9. In order to display this more simply, the tube mats 1 in FIG. 9 are shown without spacers. It is obviously possible for spacers, as described above, to be able to be provided on the tube mats 1 according to FIGS. 9 and 10. The tube mats 1 are arranged offset in relation to one another in a width direction of the tube mats 1 oriented perpendicular to the tube longitudinal axes 3. This means that the tube portions 2 of the one tube mat 1 rest on a web portion 4 of the other tube mat 1 or are at least arranged there.

Thus, this means that the tube mats 1 alternately engage in one another. The tube mats 1 are mechanically held on one another, in particular by a type of interlocking fit. As a result, an automatic fixing of the tube mats 1 to one another is produced. An active fastening, for example by gluing the individual tube mats to one another, is unnecessary.

The tube mats 1 are arranged overlapping in an overlapping region B. The overlapping region B is configured according to the embodiment shown in such a way that in each case two tube portions 2 of a tube mat 1 overlap with the respective other tube mat 1 to be connected. The overlapping region B extends in the width direction of the respective tube mat 1. It is also possible to select the overlapping region B in such a way that precisely one or three or more tube portions 2 of the tube mats 1 overlap in each case.

Figure 11:
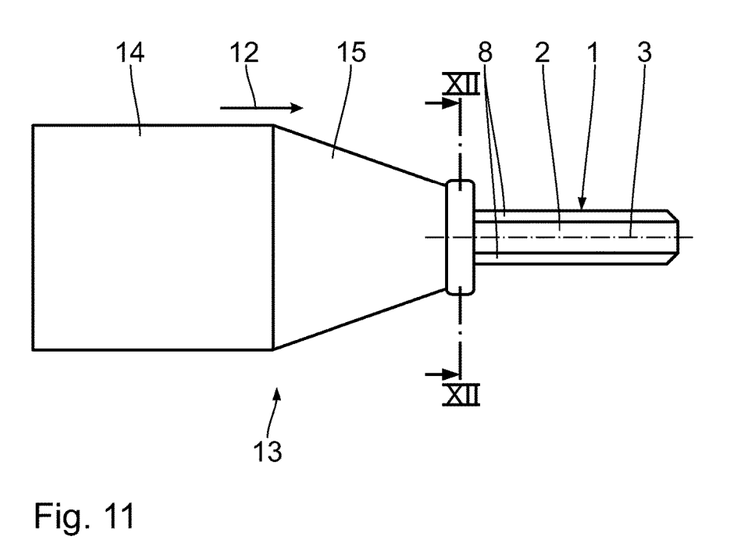
FIG. 11 shows a schematic view of a system with a tool for extruding a tube mat.
Figure 12:
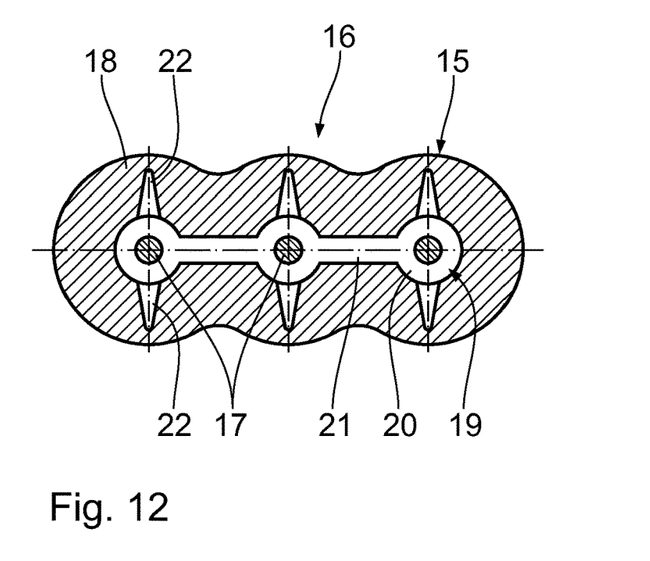
FIG. 12 shows a sectional view along line XII-XII in FIG. 11

FIGS. 11 and 12 show a device for extruding a tube mat 1 along an extrusion direction 12. The device 13 is shown schematically in FIG. 11. The device 13 comprises an extrusion chamber 14 and an extrusion nozzle 15 arranged downstream in the extrusion direction 12 and connected to the extrusion chamber 14. The extrusion chamber 14 is used to prepare a plastics material compound to be extruded. An extruder or a screw extruder for preparing plastics material granulate is used to prepare a thermoplastic compound. This takes place by heating and/or mixing the granulate in order to melt it. The plastics material melt is then fed to the extrusion nozzle 15 and the tube mat 1 is extruded by the latter along the extrusion direction 12.

To process elastomers, such as, for example, silicone, a plastic raw compound is firstly provided, which comprises monomers and cross linkers such as, for example, a catalyst or a radical starter. This raw compound is fed cold, in other words, for example, at room temperature, by means of a screw conveyor to the extrusion nozzle 15 and the tube mat 1 is extruded along the extrusion direction 12 by the latter.

After this shaping, the tube mat 1 is heated so that a thermal cross linking of the monomers takes place.

According to the embodiment shown, a tube mat 1 that can be produced with the extrusion nozzle 15 has three tube portions and two web portions arranged in between. Spacers can be formed on in one piece on an upper and lower side of the tube portions in each case. Simultaneous extrusion of a plurality of tube portions and web portions to form the tube mat 1 is made possible by the tool 16 according to the invention shown in detail in FIG. 12. Apart from the extrusion nozzle 15, the tool 16 comprises a plurality of mandrels 17. The extrusion nozzle 15 comprises a solid housing 18, in which a mat cavity 19 is provided. The mat cavity 19 comprises three tube cavities 20, in each case having a longitudinal axis and arranged parallel to the extrusion direction 12, and two web cavities 21 in each case arranged between two tube cavities 20 and connecting the tube cavities 20. The mandrel 17 is arranged in the tube cavity 20 coaxially to the respective longitudinal axis of a tube cavity 20. Furthermore, two respective spacer cavities 22 are provided on the tube cavities 20 in order to be able to form the spacers on the tube mat 1.

To produce a tube mat 1 according to the first embodiment with spacers in such a way that they have a reduced length $L_{Ab}$ along the tube longitudinal axis 3, an additional matrix, not shown in FIGS. 11 and 12, is required. This matrix has a mat cavity, which substantially corresponds to the mat cavity 19 of the extrusion nozzle 15. The mat cavity of the additional matrix does not, however, have any spacer cavities in the region of the tube cavities. The additional matrix is arranged downstream of the extrusion nozzle 15 along the extrusion direction 12. The additional matrix can be displaced along the extrusion direction 12 relative to the device 13 and, in particular, relative to the tool 16. A method of this type to extrude tubes with a variable external diameter is known from U.S. Pat. No. 5,511,965.

Figure 13:
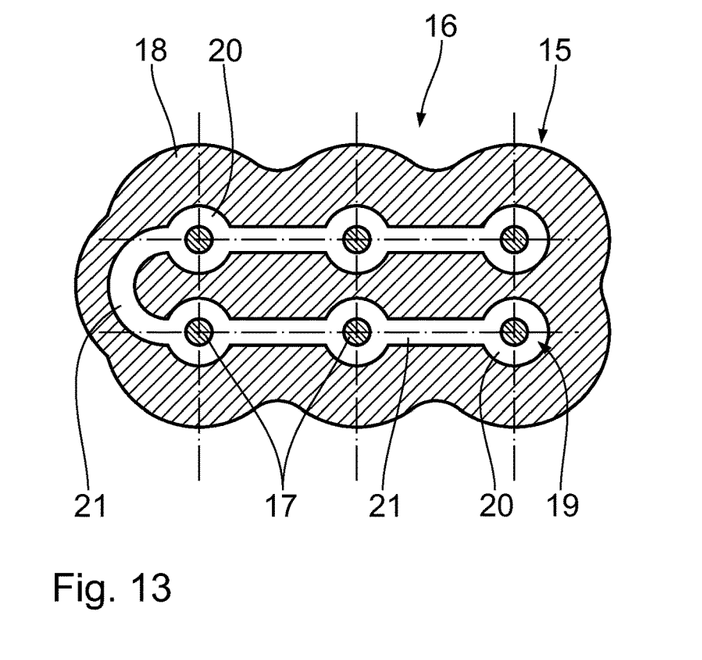
FIG. 13 shows a sectional view, corresponding to FIG. 12, of a tool according to a further embodiment.

FIG. 13 shows a further configuration of a tool 16, which is substantially identical to the tool according to FIG. 12. The important difference is the number of tube cavities 20. In total, the tool 16 according to FIG. 13 has six tube cavities 20, which are arranged in two rows of three one above the other in the tool 16. This can avoid the tool 16 being made very flat and wide. The tool 16 is very compact. The two rows of three tube cavities 20 are connected to one another by a web cavity 21, the connecting web cavity 21 being curved. The connecting web cavity 21 has a bend length along the curvature such that the length is identical to that of the remaining web cavities 21, which are provided between the tube cavities 20 arranged in a row in each case. Because of the resilient, flexible material properties of the silicone rubber, the tube mat 1 extruded with the tool 16 in FIG. 13 may be arranged flat in a mat plane 5.

Owing to the compact configuration of the tool 16, it is possible to reduce a required operating pressure for the plastics material melt or the silicone raw compound and therefore the tool closing forces when producing a tube mat 1. At the same time it is possible to effectively and advantageously produce particularly large tube mats 1, i.e. with a large number of tube portions arranged next to one another.

The invention claimed is:

1. A tube mat configured for use in an oxygenator, the tube mat comprising:
    a. a plurality of tube portions in each case having a tube longitudinal axis, wherein the tube portions are provided for fluid flow therethrough;
    b. at least one web portion connecting the two tube portions to one another; and c. at least one spacer oriented generally perpendicular to a plane of the tube mat, the at least one spacer extending outwardly beyond an outer periphery of a tube portion; and wherein the tube mat is produced in one piece by extrusion of a plastic material, and wherein the at least one spacer is arranged on part of the at least one web portion and has a length in a direction of the tube longitudinal axis that is smaller than a length of the tube portions.

2. A tube mat according to claim 1, wherein the at least one spacer has a thickness which is greater than an external diameter of the tube portion.

3. A tube mat according to claim 1, wherein the at least one spacer is arranged on a tube portion.

4. A tube mat according to claim 1, comprising a plurality of spacers disposed along the tube longitudinal axis.

5. A tube mat according to claim 1, wherein the at least one spacer has a cross sectional face, which is oriented generally perpendicular to the tube longitudinal axis and which comprises one of a circular and a star-shaped contour.

6. A tube mat according to claim 1, further comprising a plurality of recesses formed in the at least one web portion, the plurality of recesses spaced apart along a direction generally parallel to the tube longitudinal axis.

7. A tube mat according to claim 1, wherein the tube mat is produced from one of silicone rubber and polyurethane and rolled up to form a tube mat bundle.

8. A tube mat according to claim 1, wherein the at least one spacer is arranged on part of the at least one web portion extending between two adjacent tube portions.

9. A tube mat according to claim 3, wherein the at least one spacer extends outwardly from the tube portion.

10. A tube mat according to claim 4, wherein the plurality of spacers are spaced apart along the tube longitudinal axis.

11. A tube mat according to claim 1, wherein the at least one web portion has a plurality of spaced apart holes formed therein with each hole extending in a direction generally perpendicular to the tube longitudinal axis.

12. A tube mat according to claim 1, wherein each tube portion has a tube wall with a tube wall thickness between 10 µm and 200 µm.

13. A tube mat configured for use in an oxygenator, the tube mat comprising:
a. a plurality of tube portions, each one of the tube portions having a tube longitudinal axis, wherein the tube portions are provided for fluid flow therethrough;
b. at least one web portion connecting two of the tube portions to one another; and
c. at least one spacer oriented generally perpendicular to a plane of the tube mat, the at least one spacer extending outwardly beyond an outer periphery of one of the tube portions; and wherein the tube mat is produced in one piece, the at least one spacer is formed of part of the at least one web portion, the at least one spacer has a length no greater than a length of the tube portions, the at least one spacer extends lengthwise generally in a direction of the tube longitudinal axis, and the tube mat is made of one of silicone rubber and polyurethane.

14. A tube mat according to claim 13, wherein the at least one spacer comprises a plurality of spacers spaced apart in a direction generally parallel to the tube longitudinal axis.

15. A tube mat according to claim 13, wherein the at least one spacer extends outwardly from one of the tube portions in opposite directions from the one of the tube portions.

16. A tube mat according to claim 13, wherein the at least one of the spacers extends between two adjacent tube portions connected by the at least one web portion.

17. A tube mat according to claim 13, wherein the at least one web portion has a plurality of recesses formed therein extending generally transversely relative to the plane of the tube mat and which are spaced apart in a direction generally parallel to the tube longitudinal axis.

18. A tube mat according to claim 13, wherein the at least one spacer is elongate, the elongate at least one spacer extending outwardly from one of the tube portions and extending lengthwise along the tube longitudinal axis of the one of the tube portions.

19. A tube mat according to claim 13, wherein each tube portion has a tube wall with a tube wall thickness between 10 µm and 200 µm.

20. A tube mat assembly with at least one tube mat for use in an oxygenator, wherein the tube mat comprises:
a. a plurality of tube portions, each one of the tube portions having a tube longitudinal axis, wherein the tube portions are provided for fluid flow;
b. at least one web portion connecting two of the tube portions, the at least one web portion having a recess formed therein comprised of a hole; and
c. at least one spacer oriented generally perpendicular to a plane of the tube mat, the at least one spacer extending outwardly beyond the outer periphery of one of the tube portions; and wherein the tube mat is formed of one piece by extrusion of a plastic material, the at least one spacer comprises part of the at least one web portion, the at least one spacer having a length no greater than a length of the tube portions, and the at least one spacer extending lengthwise generally in the direction of the tube longitudinal axis.

21. A tube mat assembly according to claim 20, wherein the at least one web portion has a generally planar portion that extends along the plane of the tube mat and connects the two of the tube portions, and wherein the at least one recess comprises a plurality of spaced apart recesses formed in the generally planar portion of the at least one web portion.

22. A tube mat assembly according to claim 20, wherein the at least one spacer comprises a plurality of spacers spaced apart in a direction generally parallel to the tube longitudinal axis.

23. A tube mat assembly according to claim 20, further comprising a plurality of tube mats;
wherein the plurality of tube mats is rolled into a bundle along the longitudinal axes of the tube portions.

24. A tube mat assembly according to claim 23, wherein the plurality of tube portions of a first tube mat align with the plurality of spacers of a second tube mat when the plurality of tube mats is rolled into a bundle.

25. A tube mat assembly according to claim 20, wherein each tube portion has a tube wall with a tube wall thickness between 10 µm and 200 µm.

* * * * *